United States Patent
Yang et al.

(10) Patent No.: US 11,274,326 B2
(45) Date of Patent: Mar. 15, 2022

(54) POLYPHOSPHATE-DEPENDENT GLUCOKINASE AND METHOD FOR PRODUCING GLUCOSE 6-PHOSPHATE USING SAME

(71) Applicant: CJ CHEILJEDANG CORPORATION, Seoul (KR)

(72) Inventors: Sung Jae Yang, Suwon (KR); Young Mi Lee, Suwon (KR); Seong Bo Kim, Seongnam (KR); Seung Won Park, Yongin (KR); Hyun Kug Cho, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/917,389

(22) Filed: Jun. 30, 2020

(65) Prior Publication Data

US 2020/0325512 A1 Oct. 15, 2020

Related U.S. Application Data

(62) Division of application No. 16/070,253, filed as application No. PCT/KR2017/000521 on Jan. 16, 2017, now abandoned.

(30) Foreign Application Priority Data

Jan. 15, 2016 (KR) .......................... 10-2016-0005463

(51) Int. Cl.
*C12P 19/02* (2006.01)
*C12N 15/70* (2006.01)
*C12N 9/12* (2006.01)

(52) U.S. Cl.
CPC ............... *C12P 19/02* (2013.01); *C12N 9/12* (2013.01); *C12N 15/70* (2013.01); *C12Y 207/01002* (2013.01)

(58) Field of Classification Search
None
See application file for complete search history.

(56) References Cited

U.S. PATENT DOCUMENTS

| | | | |
|---|---|---|---|
| 10,752,888 B2* | 8/2020 | Yang | C12Y 302/01001 |
| 10,865,395 B2* | 12/2020 | Yang | C12P 19/02 |
| 2011/0236933 A1 | 9/2011 | Yang et al. | |
| 2015/0284756 A1* | 10/2015 | Baldwin | C12P 19/24 |
| | | | 435/99 |

FOREIGN PATENT DOCUMENTS

| | | | |
|---|---|---|---|
| CN | 104673855 A | 6/2015 | |
| EP | 3425047 A1 | 1/2019 | |
| KR | 20110028169 | 3/2011 | |
| KR | 10-1048148 B1 | 7/2011 | |
| WO | WO-2008142155 A2 * | 11/2008 | ........... C07D 309/14 |
| WO | 2015092013 A1 | 6/2015 | |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession Q1J0V7. Jun. 13, 2006 (Year: 2006).*
Klemke et al. Microbiology. Dec. 2014;160(Pt 12):2807-2819. (Year: 2014).*
Albi Tomas et al., "Two strictly polyphosphate-dependent gluco(manno) kinases from diazotrophic Cyanobacteria with potential to phosphorylate hexoses from polyphosphates", Applied Microbiology and Biotechnology, 2015, vol. 99, No. 9, pp. 3887-3900, XP035482671.
Anja Enrhardt et al., "Optimization of Cis-Acting Elements for Gene Expression from Nonviral Vectors In Vivo", Human Gene Therapy, 2003, vol. 14, pp. 215-225.
D. M. Esyunina et al., "Purification and Characterization of Recombinant Deinococcus radiodurans RNA Plymerase", Biochemistry (Moscow). 2015, pp. 1271-1278, vol. 80, No. 10, Pleiades Publishing Ltd.
Finbarr Hayes, "Transposon-Based Strategies For Microbial Functional Genomics and Proteomics", The Annual Review of Genetics, 2003, vol. 37, pp. 3-29.
GenBank: CP000359.1, Jan. 28, 2014, p. 1.
Hehuan Liao et al., "One-step purification and immobilization of thermophilic polyphosphate glucokinase from Thermobifida fusca YX: glucose-6-phosphate generation without ATP", Applied Microbiology and Biotechnology, 2012, vol. 93, No. 3, pp. 1109-1117, XP055549649.
Jin-Woo Jung et al., "Molecular Cloning and Characterization of Maltogenic Amylase from Deinococcus geothermalis", Korean Journal of Food Science and Technology, 2011, pp. 369-374, vol. 43, No. 3.
NCBI, GenBank accession No. ABF44877.1, "ROK Domain Protein [Deinococcus Geothermalis DSM 11300]", Jan. 28, 2014. p. 1.
Nelson Yew et al., "CpG-Depleted Plasmid DNA Vectors with Enhanced Safety and Long-Term Gene Expression in Vivo", Molecular Therapy, 2002, vol. 5, No. 6, pp. 731-738.

(Continued)

*Primary Examiner* — Christian L Fronda

(57) ABSTRACT

The present invention relates to a novel thermophilic and thermoresistant polyphosphate-dependent glucokinase having excellent stability, a composition comprising the same, and a method for producing glucose 6-phosphate using the same.

9 Claims, 5 Drawing Sheets

Specification includes a Sequence Listing.

(56) References Cited

OTHER PUBLICATIONS

International Search Report for International Patent Application No. PCT/KR2017/000521, dated Apr. 28, 2017.
Alba Romero-Rodriguez et al., "Biochemistry and regulatory functions of bacterial glucose kinases", Archives of Biochemistry and Biophysics, May 13, 2015, pp. 1-10, vol. 577-578, Elsevier.
Zhiying Chen et al., "Silencing of Episomal Transgene Expression by Plasmid Bacterial DNA Elements in Vivo", Gene Therapy, 2004, vol. 11, pp. 856-864.
Hotaro Tanaka et al., "Strictly Polyphosphate-Dependent Glucokinase in a Polyphosphate-Accumulating Bacterium, Microlunatus phosphovorus", Journal of Bacteriology, vol. 185, No. 18, Sep. 30, 2003, pp. 5654-5656.

* cited by examiner

[FIG. 1]
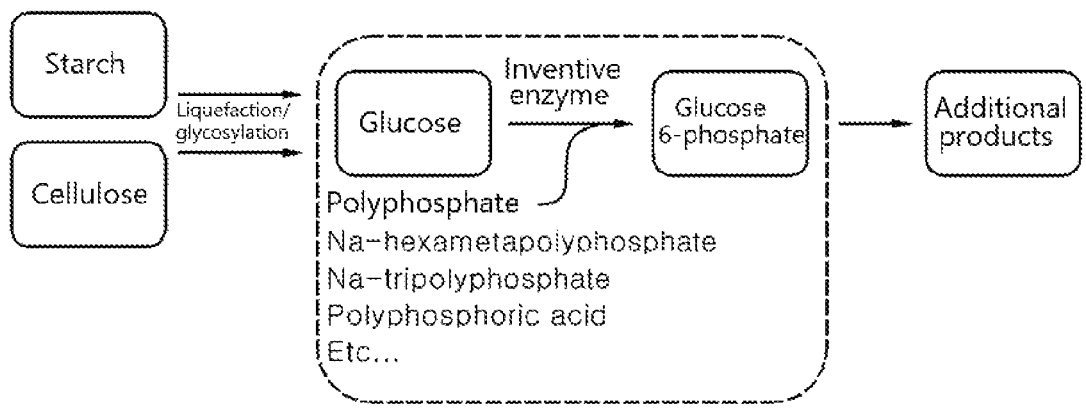
[FIG. 2]
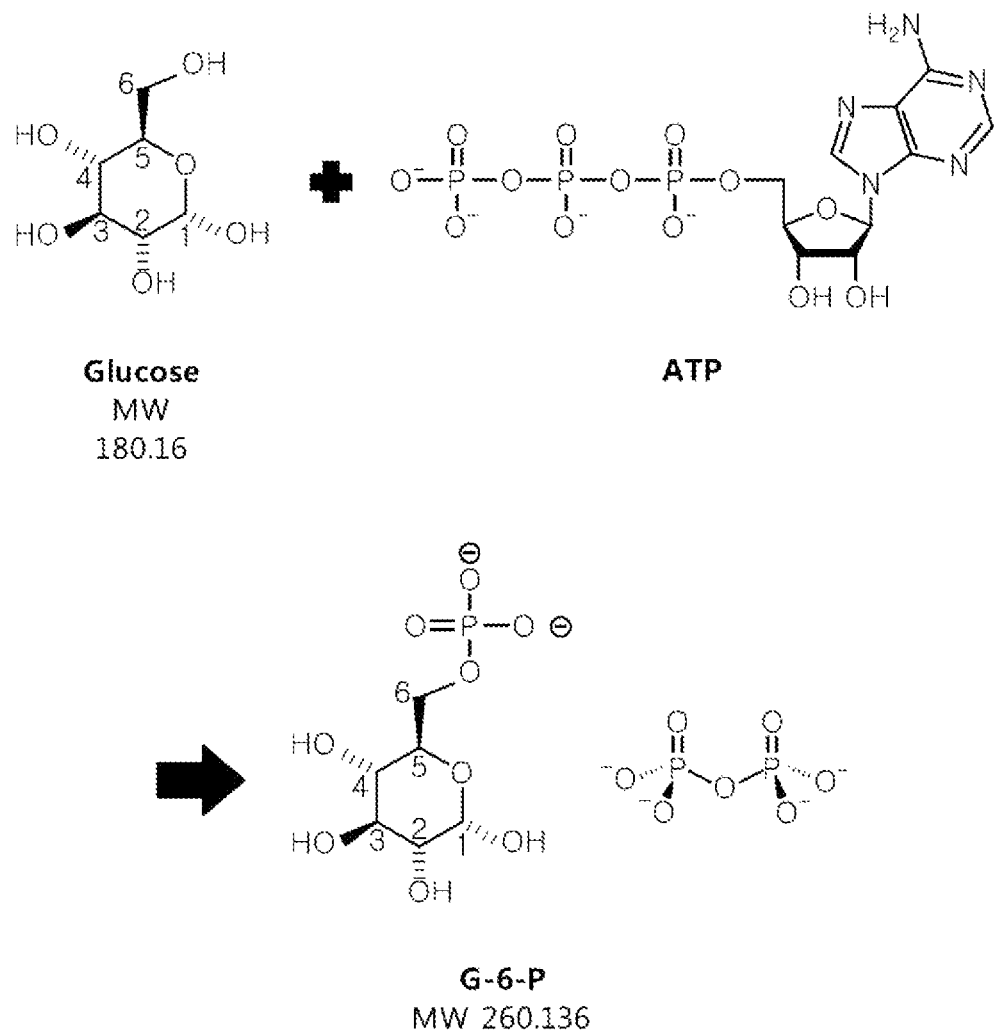

[FIG. 3]
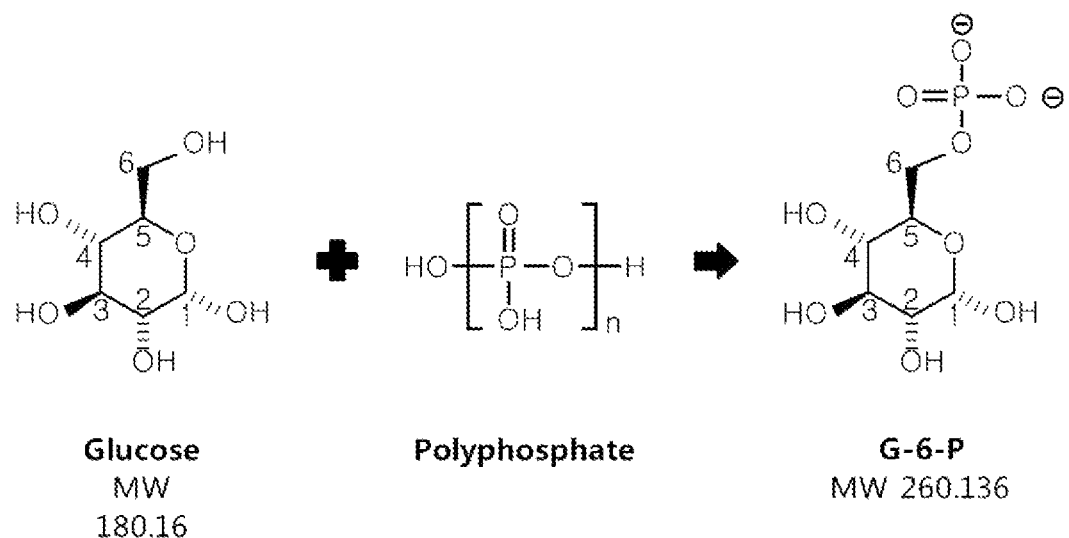
[FIG. 4]
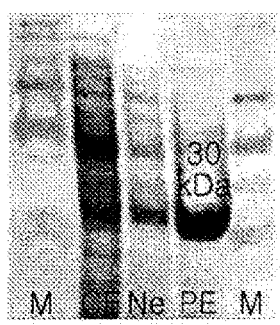

[FIG. 5]
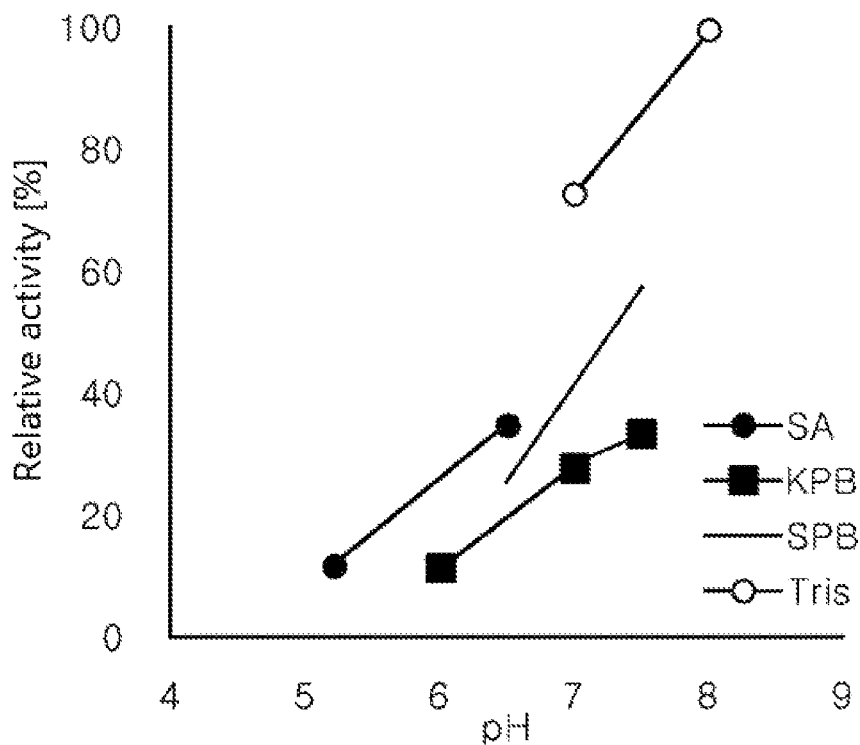
[FIG. 6]
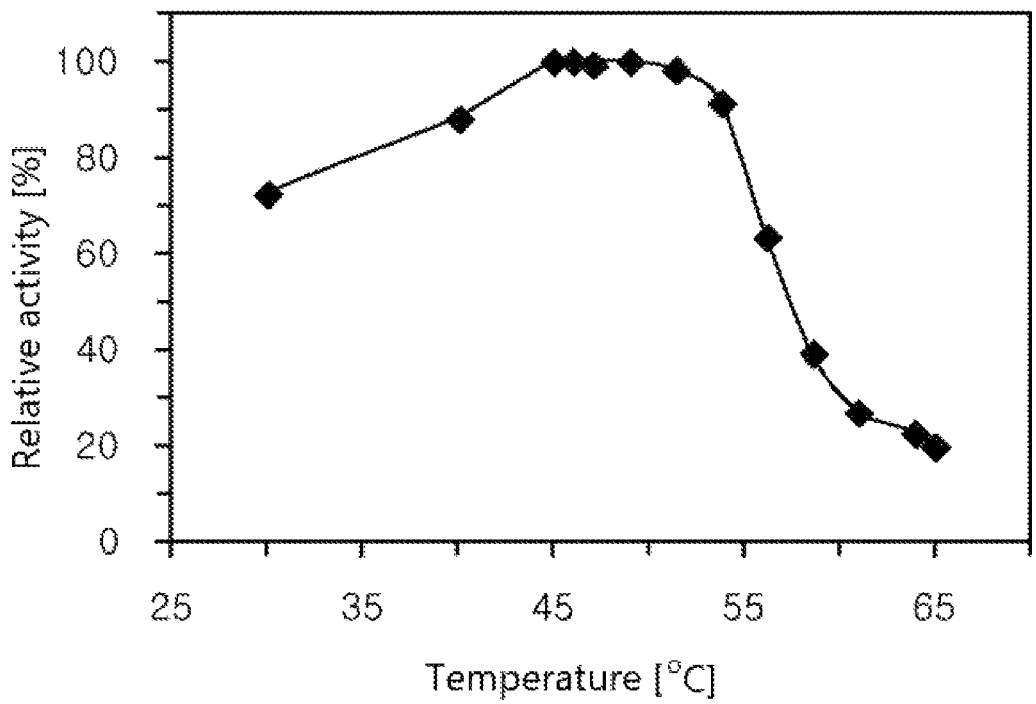

[FIG. 7]
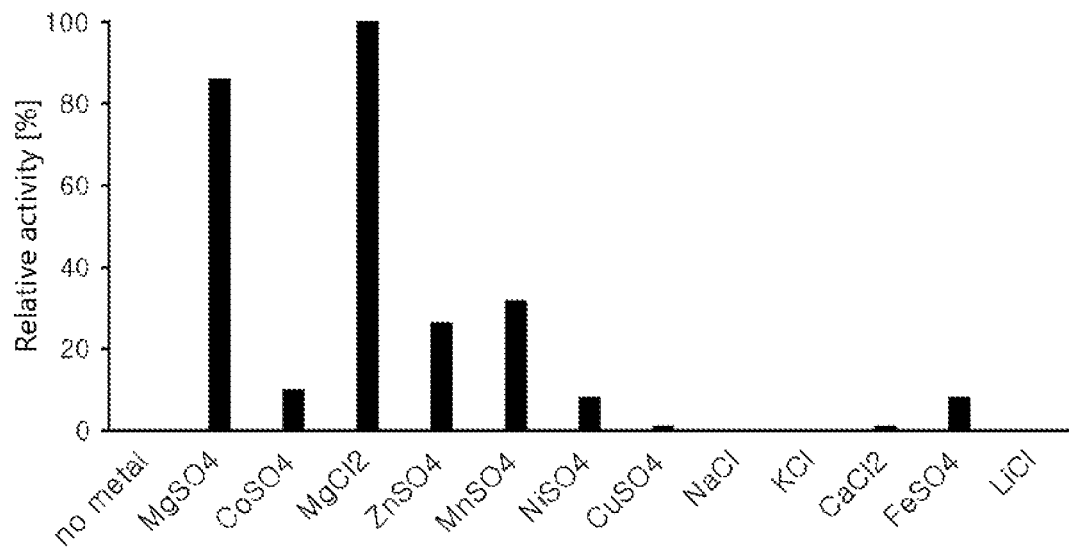
[FIG. 8]
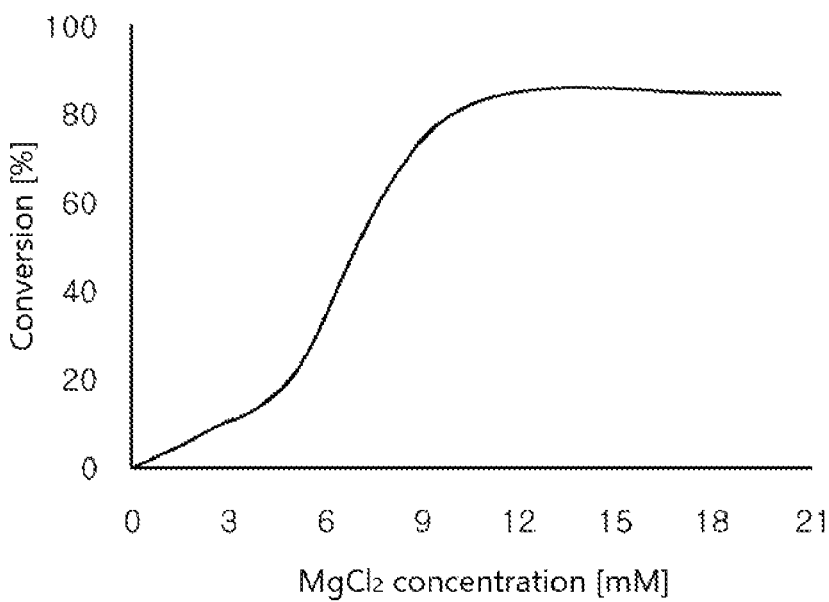

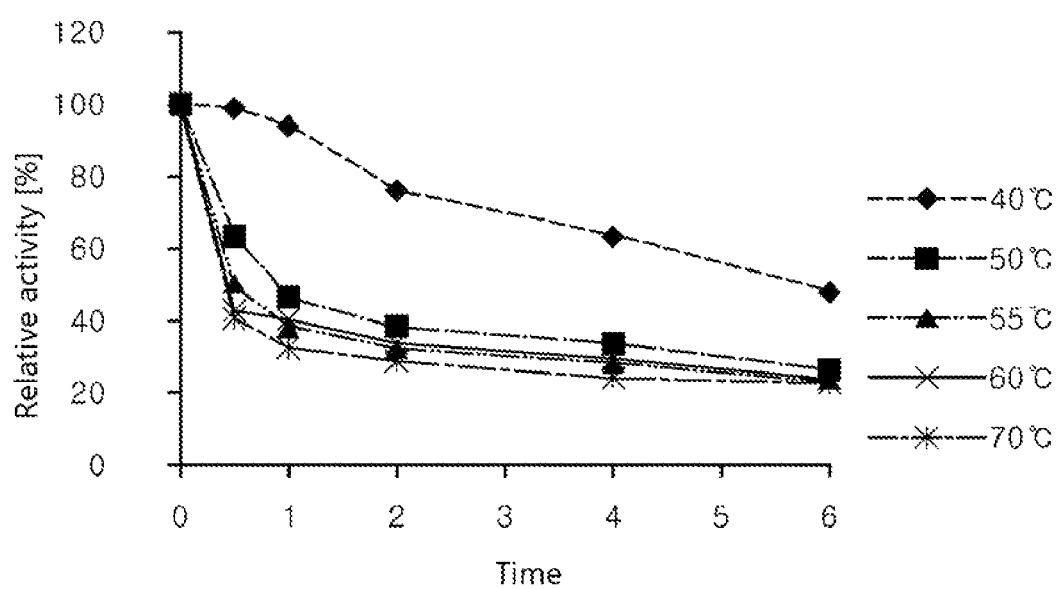
[FIG. 9]

SEQUENCE LISTING

<160> NUMBER OF SEQ ID NOS: 4

<210> SEQ ID NO 1
<211> LENGTH: 813
<212> TYPE: DNA
<213> ORGANISM: Unknown
<220> FEATURE:
<223> OTHER INFORMATION: Deinococcus geothermalis

<400> SEQUENCE: 1

```
atgctggcag ccagtgacag cagccagcat ggcgggaagg ctgttacgct atctcccatg    60
agcgtgatcc tcgggattga cataggtggg agcggcatca agggggcccc tgtggacacg   120
gcaaccggga agctggtggc cgagcgccac cgcatcccca cgcccgaggg cgcgcaccca   180
gacgcggtga aggacgtggt ggttgagctg gtgcggcatt ttgggcatgc ggggccagtc   240
ggcatcactt tccctggcat cgtgcagcac ggccataccc tgagcgcagc caatgtggat   300
aaagcctgga ttggcctgga cgccgacacg cttttactg aggcgaccgg tcgcgacgtg    360
accgtgatca cgacgcaga tgccgcgggg ctagcggagg cgaggttcgg ggccggggca    420
ggtgtgccgg gcgaggtgtt gctgttgacc tttgggacag catcggcag cgcgctgatc    480
tataacggcg tgctggtgcc caacaccgag tttgggcatc tgtatctcaa gggcgacaag   540
cacgccgaga tgggcgtc cgaccgggcc cgtgagcagg cgacctgaa ctggaagcag     600
tgggccaaac gggtcagccg gtacctccag tatctggaag gtctcttcag tcccgatctc   660
tttatcatcg gtggggcgt gagcaagaag gccgacaagt ggcagccgca cgtcgcaaca   720
acacgtaccc gcctggtgcc cgctgccctc cagaacgagg ccggaatcgt ggggccgcg   780
atggtggcgg cgcagcggtc acaggggac taa                                813
```

<210> SEQ ID NO 2
<211> LENGTH: 270
<212> TYPE: PRT
<213> ORGANISM: Unknown
<220> FEATURE:
<223> OTHER INFORMATION: Deinococcus geothermalis

<400> SEQUENCE: 2

```
Met Leu Ala Ala Ser Asp Ser Ser Gln His Gly Gly Lys Ala Val Thr
  1               5                  10                  15

Leu Ser Pro Met Ser Val Ile Leu Gly Ile Asp Ile Gly Gly Ser Gly
             20                  25                  30

Ile Lys Gly Ala Pro Val Asp Thr Ala Thr Gly Lys Leu Val Ala Glu
         35                  40                  45

Arg His Arg Ile Pro Thr Pro Glu Gly Ala His Pro Asp Ala Val Lys
     50                  55                  60

Asp Val Val Glu Leu Val Arg His Phe Gly His Ala Gly Pro Val
 65                  70                  75                  80

Gly Ile Thr Phe Pro Gly Ile Val Gln His Gly His Thr Leu Ser Ala
                 85                  90                  95

Ala Asn Val Asp Lys Ala Trp Ile Gly Leu Asp Ala Asp Thr Leu Phe
            100                 105                 110

Thr Glu Ala Thr Gly Arg Asp Val Thr Val Ile Asn Asp Ala Asp Ala
        115                 120                 125

Ala Gly Leu Ala Glu Ala Arg Phe Gly Ala Gly Ala Val Pro Gly
    130                 135                 140

Glu Val Leu Leu Leu Thr Phe Gly Thr Gly Ile Gly Ser Ala Leu Ile
145                 150                 155                 160

Tyr Asn Gly Val Leu Val Pro Asn Thr Glu Phe Gly His Leu Tyr Leu
                165                 170                 175

Lys Gly Asp Lys His Ala Glu Thr Trp Ala Ser Asp Arg Ala Arg Glu
            180                 185                 190

Gln Gly Asp Leu Asn Trp Lys Gln Trp Ala Lys Arg Val Ser Arg Tyr
        195                 200                 205
```

```
Leu Gln Tyr Leu Glu Gly Leu Phe Ser Pro Asp Leu Phe Ile Ile Gly
    210                 215                 220

Gly Gly Val Ser Lys Lys Ala Asp Lys Trp Gln Pro His Val Ala Thr
225                 230                 235                 240

Thr Arg Thr Arg Leu Val Pro Ala Ala Leu Gln Asn Glu Ala Gly Ile
                245                 250                 255

Val Gly Ala Ala Met Val Ala Ala Gln Arg Ser Gln Gly Asp
                260                 265                 270

<210> SEQ ID NO 3
<211> LENGTH: 31
<212> TYPE: DNA
<213> ORGANISM: Artificial Sequence
<220> FEATURE:
<223> OTHER INFORMATION: Forward Primer for SEQ ID (1)

<400> SEQUENCE: 3
ctgacatatg ctggcagcca gtgacagcag c                              31

<210> SEQ ID NO 4
<211> LENGTH: 31
<212> TYPE: DNA
<213> ORGANISM: Artificial Sequence
<220> FEATURE:
<223> OTHER INFORMATION: Reverse Primer for SEQ ID (1)

<400> SEQUENCE: 4
ctgacatatg ctggcagcca gtgacagcag c                              31
```

POLYPHOSPHATE-DEPENDENT GLUCOKINASE AND METHOD FOR PRODUCING GLUCOSE 6-PHOSPHATE USING SAME

CROSS-REFERENCE TO RELATED APPLICATIONS

The present specification is a divisional application of U.S. patent application Ser. No. 16/070,253, filed on Jul. 13, 2018, which is U.S. National Stage Entry of International Patent Application No. PCT/KR2017/000521 filed Jan. 16, 2017, which claims priority to and the benefit of Korean Patent Application No. 10-2016-0005463 filed in the Korean Intellectual Property Office on Jan. 15, 2016, the entire contents of which are incorporated herein by reference.

TECHNICAL FIELD

The present invention relates to a novel polyphosphate-dependent glucokinase, a composition comprising the glucokinase, and methods for producing glucose 6-phosphate using the glucokinase.

BACKGROUND ART

D-glucose 6-phosphate is a major phosphorylation product of the glycolysis pathway and the pentose phosphate pathway in the biological metabolism. D-glucose 6-phosphate is industrially very useful because it can be converted into various metabolites. The development of economic methods for producing glucose 6-phosphate is of great importance in biological processes for producing high value-added compounds from glucose 6-phosphate through a series of multiple enzymatic reactions.

According to previously published reports, glucose as a raw material, adenosine diphosphate (ADP) as a phosphate donor, and an ADP-dependent glucokinase (EC 2.7.1.147); glucose as a raw material, adenosine triphosphate (ATP) as a phosphate donor, and an ATP-dependent glucokinase (EC 2.7.1.2); or glucose as a raw material, polyphosphate (Poly$(Pi)_n$) as a phosphate polymer, and a polyphosphate (poly$(Pi)_n$)-dependent glucokinase (EC 2.7.1.63) are used to directly enzymatically produce glucose 6-phosphate.

According to the method using an ADP/ATP-dependent glucokinase, the phosphate groups of ADP or ATP are transferred to glucose to produce glucose 6-phosphate (see Reaction Scheme 1). The method is disadvantageous in that ADP and ATP are expensive. In an attempt to overcome the disadvantage, a polyphosphate-AMP/ADP phosphotransferase and Poly$(Pi)_n$ as a material donating the phosphate groups to AMP or ADP are simultaneously used to recover ADP or ATP. However, this attempt is limited in practical use due to the poor stability of AMP, ADP, and ATP.

[Reaction Scheme 1]

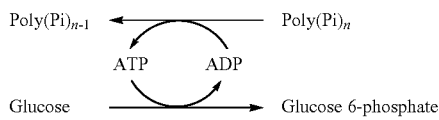

According to the method using a polyphosphate-dependent glucokinase, the phosphate groups of Poly$(Pi)_n$ are transferred to glucose to directly produce glucose 6-phosphate (see Reaction Scheme 2). The use of inexpensive stable Poly$(Pi)_n$ makes this method advantageous from the viewpoint of economic efficiency over the method using an ADP/ATP-dependent glucokinase.

[Reaction Scheme 2]

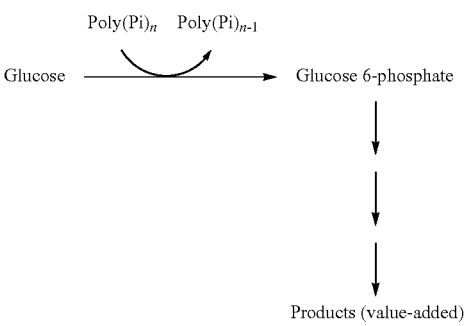

DISCLOSURE

The Sequence Listing created on Jul. 13, 2018 with a file size of 4 KB, and filed herewith in ASCII text file format as the file entitled "42D7310.TXT," is hereby incorporated by reference in its entirety.

Technical Problem

The present invention is directed to a novel polyphosphate-dependent glucokinase, a composition comprising the glucokinase, and methods for producing glucose 6-phosphate using the glucokinase. The stability of an enzyme is a very important requirement in terms of efficiency for the enzymatic production of a specific compound. To date, however, a limited number of polyphosphate-dependent glucokinases in connection with the present invention have been reported in some microbial species. Most of the isolated enzymes were derived from mesophilic microorganisms and were reported to have poor characteristics such as low thermal stability (Table 1). The present invention has been made in an effort to solve the above problems, and it is one object of the present invention to provide a novel thermophilic and thermoresistant polyphosphate-dependent glucokinase with good stability derived from a thermophile, a composition comprising the enzyme, and methods for producing glucose 6-phosphate using the enzyme.

TABLE 1

| Microorganism | Optimum temp. & thermal stability | Reference |
|---|---|---|
| *Mycobacterium phlei* | NA | 1957. Bull Acad Pol Sci Ser Sci Biol. 5: 379-381 |
| | NA | 1964. Biochem Biophys Acta. 85: 283-295 |

TABLE 1-continued

| Microorganism | Optimum temp. & thermal stability | Reference |
|---|---|---|
| Corynebacterium diphtheria | NA | 1961. Bull Acad Pol Sci Ser Sci Biol. 9: 371-372 |
| Mycobacteria | NA | 1978. Acta Microbiol Pol. 27: 73-74 |
| Nocardia minima | NA | 1979. Acta Microbiolog Pol. 28: 153-160 |
| Propionibacterium shermanii | NA | 1986. J Bio Chem. 261: 4476-4480 |
| Mycococcus coralloudes | NA | 1990. Arch Microbiology 154: 438-442 |
| Mycobacterium tuberculosis | NA | 1996. Biochemistry. 35: 9772-81. |
| Microlunatus phosphovorus | Optimum temp.: 30° C. | 2003. J Bacteriol. 185: 5654-5656 |
| Arthrobacter sp. KM | 40° C. 5 min, 50% of its activity was lost Optimum temp.: 30° C. | 2003. Appl Environ Microbiol. 69: 3849-3857 2004. J Biol Chem 279: 50591-50600 |
| Corynebacterium glutamicum | 50° C. 60 min, 88% of its activity was lost | 2010. Appl Microbiol Biotechnol. 87: 703-713 |
| Thermobifida fusca | 50° C. 25 min, 50% of its activity was lost | 2011 Appl Microbiol Biotechnol. 93: 1109-1117 |
| Straptomyces coelicolor A3(2) | Optimum temp.: 25° C. | 2013 Biosci Biotechnol Biochem. 77: 2322-2324 |
| Anabaena sp. PCC 7120 | Optimum temp.: 28° C. | 2014. Microbiology. 160: 2807-2819 |

Glucose 6-phosphate is a major phosphorylation product of the glycolysis pathway and the pentose phosphate pathway in the biological metabolism. D-glucose 6-phosphate is industrially very useful because it can be converted into various metabolites. Economic methods for producing glucose 6-phosphate are necessary to produce high value-added compounds from glucose 6-phosphate through a series of multiple enzymatic reactions.

ATP or ADP is usually used as a phosphate donor for enzymatic conversion of glucose to glucose 6-phosphate in the biological metabolism and its high commercial price is an obstacle to the development of processes for enzymatic production of glucose 6-phosphate via the reaction pathway. Further, microbial fermentation is not suitable for the production of glucose 6-phosphate because the resulting glucose 6-phosphate does not cross cell membranes.

Polyphosphate (Poly(Pi)$_n$) as a phosphate donor is plentiful in nature or can be economically produced by chemical processes and is thus considered a commercially valuable compound. It can be concluded that the development of an efficient method for enzymatic production of glucose 6-phosphate from glucose using Poly(Pi)$_n$ is commercially very important.

However, most of the previously reported enzymes for glucose 6-phosphate production using Poly(Pi)$_n$ react at low temperature and have poor thermal stability, limiting their application to the production of glucose 6-phosphate.

Technical Solution

The present invention is aimed at providing a novel thermophilic and thermoresistant polyphosphate-dependent glucokinase with good stability derived from a thermophilic organism and methods for producing glucose 6-phosphate using the enzyme.

Numerous aspects of the present invention will now be described in detail.

One aspect of the present invention provides a thermoresistant polyphosphate-dependent glucokinase derived from the genus *Deinococcus*.

Specifically, the polyphosphate-dependent glucokinase according to the present invention may have the amino acid sequence set forth in SEQ ID NO. 2. The polyphosphate-dependent glucokinase may be any protein that has an amino acid sequence having a homology of at least 70%, specifically at least 80%, more specifically at least 90%, even more specifically at least 95% to the amino acid sequence set forth in SEQ ID NO. 2 and has an enzymatic activity substantially identical or similar to that of the enzyme. That is, a protein variant whose amino acid sequence has a homology to the amino acid sequence set forth in SEQ ID NO. 2 and is partially deleted, modified, substituted or added is also within the scope of the present invention as long as its amino acid sequence substantially exhibits the function of polyphosphate-dependent glucose phosphorylation.

As used herein, the term "homology" refers to the degree of identity or correspondence between given polypeptide sequences or polynucleotide sequences that may or may not share a common evolutionary origin and may be expressed as a percentage. In the present specification, a homology sequence having an identical or similar activity to a given polypeptide or polynucleotide sequence is expressed as "% homology". For example, the homology may be determined using a standard software, specifically BLAST 2.0, to calculate parameters such as score, identity, and similarity. Alternatively, the homology may be identified by comparing sequences in a Southern hybridization experiment under defined stringent conditions. The defined appropriate hybridization conditions may be determined by methods well known to those skilled in the art (see Sambrook et al., 1989, infra). In one embodiment, two amino acid sequences are judged to be "substantially homologous" or "substantially similar" when at least 21% (specifically at least about 50%, particularly about 90%, 95%, 96%, 97% or 99%) of the polypeptides match over the defined length of the amino acid sequences.

Another aspect of the present invention provides a polynucleotide encoding a thermoresistant polyphosphate-dependent glucokinase derived from the genus *Deinococcus*. Specifically, the polynucleotide encodes a protein having the activity of a polyphosphate-dependent glucokinase having the amino acid sequence set forth in SEQ ID NO. 2.

As used herein, the term "polynucleotide" refers to a polymer of nucleotide units that are linked covalently to form a long chain. Generally, the polynucleotide means a DNA or RNA strand whose length is above a predetermined level.

The polynucleotide encoding a protein having the activity of a polyphosphate-dependent glucokinase may include a polynucleotide sequence encoding the amino acids shown in SEQ ID NO. 2. Various modifications may be made in the coding region of the polynucleotide as long as the amino acid sequence of the polypeptide is not altered due to the degeneracy of codons or in consideration of preferential codons in an organism where the enzyme is to be expressed. For example, the polynucleotide may have the sequence set forth in SEQ ID NO. 1. The polynucleotide may have a nucleotide sequence having a homology of at least 70%, specifically at least 80%, more specifically at least 90%, even more specifically at least 95%, most specifically at least 98% to the sequence set forth in SEQ ID NO. 1 and can substantially encode a protein having a polyphosphate-dependent glucose phosphorylation activity. It is apparent that a variant whose amino acid sequence is partially deleted, modified, substituted or added is also within the scope of the present invention.

A composition comprising 1% to 3% by weight of glucose, 1% to 10% by weight of polyphosphate, 0.1 mg/ml to 2.0 mg/ml of the polyphosphate-dependent glucokinase, and optionally 1 mM to 20 mM magnesium ions (e.g., $MgCl_2$) based on the total volume of the composition can achieve a conversion yield of at least 60%, more specifically at least 70%, even more specifically at least 80%, to glucose 6-phosphate.

A composition comprising 1.5% by weight of glucose, 3% by weight of polyphosphate, 0.3 mg/ml of the polyphosphate-dependent glucokinase, and 10 mM magnesium ions (e.g., $MgCl_2$) can achieve a conversion yield of at least 60%, more specifically at least 70%, even more specifically at least 80%, to glucose 6-phosphate.

A composition comprising 5% to 20% by weight of glucose, 5% to 10% by weight of polyphosphate, 0.1 mg/ml to 2.0 mg/ml of the polyphosphate-dependent glucokinase, and 1 mM to 20 mM magnesium ions (e.g., $MgCl_2$) based on the total volume of the composition can achieve a conversion yield of at least 50%, more specifically at least 60%, even more specifically at least 70%, to glucose 6-phosphate.

A composition comprising 15% by weight of glucose, 7.5% by weight of polyphosphate, 0.3 mg/ml of the polyphosphate-dependent glucokinase, and 10 mM magnesium ions (e.g., $MgCl_2$) can achieve a conversion yield of at least 50%, more specifically at least 60%, even more specifically at least 70%, to glucose 6-phosphate.

The polyphosphate-dependent glucokinase may be active at a temperature of 40° C. to 60° C., more specifically 45° C. to 55° C., most specifically 50° C.

The polyphosphate-dependent glucokinase may be active at a pH of 7 to 9, most specifically 8.

The activity of the polyphosphate-dependent glucokinase may be enhanced in the presence of magnesium ions.

The magnesium ions may be specifically present at a concentration of 1 mM to 20 mM, more specifically 5 mM to 15 mM, even more specifically 5 mM to 15 mM, most specifically 10 mM.

A further aspect of the present invention provides a composition for the production of glucose 6-phosphate comprising the polyphosphate-dependent glucokinase, glucose, and polyphosphate. The composition may further comprise magnesium ions. The ingredients used in this aspect and their contents are the same as those described in the previous and following aspects, and a detailed description thereof is thus omitted.

Yet another aspect of the present invention provides a method for producing glucose 6-phosphate from a composition comprising the polyphosphate-dependent glucokinase, glucose, and polyphosphate.

The reaction for the production of glucose 6-phosphate is carried out at a temperature of 40° C. to 60° C. and a pH of 7 to 9.

The glucose may be prepared by liquefaction or glycosylation of starch or cellulose.

The polyphosphate serves as a phosphate donor, and examples thereof include, but are not limited to, sodium hexametaphosphate, sodium tripolyphosphate, and potassium hexametaphosphate, which are also commercially available.

The glucose 6-phosphate may be produced at a temperature of 40° C. to 60° C., more specifically 45° C. to 55° C., most specifically 50° C.

The polyphosphate-dependent glucokinase may have a molecular weight of 10 kDa to 100 kDa, specifically 20 kDa to 50 kDa.

The composition may further comprise magnesium ions. For example, a source of the magnesium ions may be $MgCl_2$ or $MgSO_4$.

The polyphosphate-dependent glucokinase may be present in an amount of 0.1 mg to 0.5 mg, more specifically 0.2 mg to 0.4 mg, most specifically 0.3 mg per ml of the composition.

The glucose may be present in an amount of 1% to 30% by weight, more specifically 1% to 20% by weight, most specifically 3% to 15% by weight, based on the total weight of the composition.

The polyphosphate may be present in an amount of 1% to 15% by weight, more specifically 1% to 10% by weight, most specifically 1.5% to 7.5% by weight, based on the total weight of the composition.

Yet another aspect of the present invention provides a method for enhancing the activity of the polyphosphate-dependent glucokinase on the conversion of glucose to glucose 6-phosphate by the addition of magnesium ions.

The magnesium ions may be specifically added at a concentration of 1 mM to 20 mM, more specifically 5 mM to 15 mM, even more specifically 10 mM in a composition for the production of glucose 6-phosphate.

A source of the magnesium ions may be $MgCl_2$ or $MgSO_4$. Any magnesium salt capable of providing magnesium ions to the composition may be used without limitation.

Yet another aspect of the present invention provides a method for producing glucose 6-phosphate from a composition comprising the polyphosphate-dependent glucokinase, a diastatic enzyme, starch, and polyphosphate.

The reaction for the production of glucose 6-phosphate is carried out at a temperature of 40° C. to 60° C. and a pH of 7 to 9.

The diastatic enzyme may be selected from alpha-amylases, glucoamylases, alpha-glycosidases, and mixtures thereof.

Yet another aspect of the present invention provides a microorganism producing the polyphosphate-dependent glucokinase. Specifically, the microorganism belongs to the genus *Escherichia*, for example, *Escherichia coli*, but not limited thereto.

As used herein, the term "microorganism producing the polyphosphate-dependent glucokinase" refers to a prokaryotic or eukaryotic microbial strain that can produce the enzyme therein. Specifically, the microorganism producing the polyphosphate-dependent glucokinase is a microorganism capable of accumulating the enzyme in a medium or therein by genetic engineering or natural mutation.

The microorganism is not specifically limited and may be any one that can express the polypeptide having the sequence set forth in SEQ ID NO. 2. The microorganism may be a prokaryotic or eukaryotic microorganism, specifically a prokaryotic microorganism. Examples of such prokaryotic microorganisms include, but are not limited to, microbial strains belonging to the genera *Escherichia, Erwinia, Serratia, Providencia, Corynebacterium,* and *Brevibacterium*. Specifically, the microorganism may be one belonging to the genus *Escherichia*.

As used herein, the term "expression" refers to a process in which a polynucleotide encoding the polypeptide of the present invention is operably transformed with a recombinant vector or is inserted into a chromosome. The expression process is not particularly limited.

As used herein, the term "transformation" refers to the introduction of a vector including a polynucleotide encoding a target protein into a host cell to express the protein encoded by the polynucleotide in the host cell. The transformed polynucleotide may be either inserted into and located in the chromosome of the host cell or may exist extrachromosomally as long as it can be expressed in the host cell. The polynucleotide includes DNA and RNA encoding the target protein. The polynucleotide may be introduced in any form as long as it can be introduced into and expressed in the host cell. For example, the polynucleotide may be introduced into the host cell in the form of an expression cassette, which is a gene construct including all elements required for its autonomous expression, but its form is not limited thereto. Typically, the expression cassette includes a promoter operably linked to the polynucleotide, a transcription termination signal, a ribosome-binding domain, and a translation termination signal. The expression cassette may be in the form of a self-replicable expression vector. The polynucleotide as it is may be introduced into the host cell and operably linked to sequence required for expression in the host cell.

As used herein, the term "operably linked" refers to a functional linkage between a promoter sequence initiating and mediating the transcription of the polynucleotide encoding the target protein of the present invention and a gene sequence.

As used herein, the term "vector" refers to any vehicle for the cloning of and/or transfer of bases into a host cell. A vector may be a replicon to which another DNA segment may be attached so as to bring about the replication of the attached segment. A "replicon" refers to any genetic element (e.g., plasmid, phage, cosmid, chromosome or virus) that functions as an autonomous unit of DNA replication in vivo, i.e. capable of replication under its own control. The term "vector" may include both viral and nonviral vehicles for introducing bases into a host cell in vitro, ex vivo or in vivo. The term "vector" may also include minicircle DNAs. For example, the vector may be a plasmid without bacterial DNA sequences. The removal of bacterial DNA sequences which are rich in CpG regions has been shown to decrease transgene expression silencing and result in more persistent expression from plasmid DNA vectors (e.g., Ehrhardt, A. et al. (2003) HumGene Ther 10: 215-25; Yet, N. S. (2002) Mol Ther 5: 731-38; Chen, Z. Y. et al. (2004) Gene Ther 11: 856-64). The term "vector" may also include transposons (Annu Rev Genet. 2003; 37:3-29), or artificial chromosomes. Specific examples of vectors suitable for use in the present invention include, but are not limited to, pACYC177, pACYC184, pCL1920, pECCG117, pUC19, pBR322, and pMW118 vectors. Variants of these vectors, for example, in which promoters are mutated, may also be used in the present invention.

Particularly, the vector may be a DMA construct including a polynucleotide sequence encoding the desired protein which is operably linked to an appropriate expression regulatory sequence to express the desired protein in a suitable host cell. The regulatory sequence may include a promoter that can initiate transcription, an optional operator sequence for regulating the transcription, a sequence encoding a suitable mRNA ribosome binding site, and a sequence regulating the termination of transcription and translation. After the vector is introduced into the suitable host cell, it may replicate or function independently of the host genome and may be integrated into the genome itself.

The vector used in the present invention is not particularly limited as long as the vector is replicable in the host cell. The vector may be any of those known in the art. Examples of such known vectors include natural or recombinant plasmids, cosmids, viruses, and bacteriophages. The phage vectors or cosmid vectors may be, for example, pWE15, M13, λWE15, λ E15, E15, M13, and Charon21A, but are not limited thereto. The plasmid vectors may be those based on pBR, pUC, pBluescriptII, pGEM, pTZ, pCL, and pET, but are not limited thereto.

The present invention also provides a recombinant expression vector including a gene encoding the polyphosphate-dependent glucokinase.

The present invention also provides *Escherichia coli* BL21 DE3 CJ pET21a-Dg_ppgk transformed with the recombinant expression vector. The strain was deposited with the Korean Culture Center of Microorganisms on Dec. 17, 2015 under the deposit number KCCM11793P.

The present invention also provides economic methods for producing industrially useful compounds from polyphosphate and glucose or starch based on one-pot enzymatic conversions using the polyphosphate-dependent glucokinase and additional functional enzymes (e.g., α-amylases, glucoamylases, α-glucosidases, isomerases, aldolases, synthases, kinases, and phosphatases).

Examples of such industrially useful compounds include, but are not limited to, D-glucose 1-phosphate, D-fructose 6-phosphate, D-fructose 1,6-bisphosphate, myo-inositol 3-phosphate, myo-inositol, D-glucuronate, D-glucosamine 6-phosphate, D-glucosamine, N-acetyl-D-glucosamine 6-phosphate, N-acetyl-D-glucosamine, N-acetyl-D-mannosamine 6-phosphate, N-acetyl-D-mannosamine, N-acetyl-neuraminic acid (sialic acid), D-mannose 6-phosphate, D-mannose, D-tagatose 6-phosphate, D-tagatose, D-allulose 6-phosphate, D-allulose, D-glyceraldehyde 3-phosphate, and dihydroxyacetone phosphate. The industrially useful compounds may also include various compounds produced from glucose 6-phosphate.

Advantageous Effects

The enzyme according to the present invention can participate in an enzymatic reaction at a high temperature. The high reaction temperature increases the solubility of Poly (Pi)$_n$ and glucose as substrates, enabling the use of the substrates at high concentrations. In addition, the diffusion rates of the materials and the reaction rate can be increased and the reaction time can be reduced, achieving increased unit productivity. Furthermore, the high reaction temperature can minimize contamination caused by foreign microorganisms during processing. Moreover, the enzyme according to the present invention can be heated to a high temperature after large-scale recombinant expression in a mesophile due to its good heat resistance, enabling selective modification and removal of other proteins derived from the mesophile.

DESCRIPTION OF DRAWINGS

FIG. 1 is a flowchart illustrating a method for producing glucose 6-phosphate according to the present invention.

FIG. 2 shows a reaction scheme for the production of glucose 6-phosphate from ATP and glucose.

FIG. 3 shows a reaction scheme for the production of glucose 6-phosphate from polyphosphate and glucose.

FIG. 4 shows SDS-PAGE gel images of a size marker (M), a crude extract (CE) after cell destruction, an enzyme whose gene expression was not induced as a negative control (Ne), and a purified enzyme (PE) after gene expression, which were taken after electrophoresis.

FIG. 5 shows the pH-dependent activity of a recombinant polyphosphate-dependent glucokinase.

FIG. 6 shows the temperature-dependent activity of a recombinant polyphosphate-dependent glucokinase.

FIG. 7 shows the activities of a recombinant polyphosphate-dependent glucokinase in the presence of different kinds of metal ions.

FIG. 8 shows the activities of a polyphosphate-dependent glucokinase at different concentrations of $MgCl_2$.

FIG. 9 shows the activities of a polyphosphate-dependent glucokinase when heated to different temperatures.

MODE FOR INVENTION

Glucose is a relatively cheap carbon source and can be mass-produced from starch or cellulose. Glucose is currently used as a basic raw material in chemical or biological conversion processes for the production of various compounds that are useful in the chemical, pharmaceutical, cosmetic, and food industries.

However, phosphorylated glucose as a basic raw material in biological processes, particularly enzymatic conversion processes, is currently limited in use due to high price thereof.

Glucose 6-phosphate is an industrially pivotal metabolite in glucose metabolism and can be used as a basic raw material that can induce very useful reactions based on the use of various metabolic enzymes present in nature (organisms).

Under these circumstances, the present invention is aimed at providing an enzyme and economic enzymatic methods for producing glucose 6-phosphate, which is a raw material for various industrially useful compounds, from glucose and polyphosphate.

The present invention is also aimed at providing high value-added functional compounds in the pharmaceutical, cosmetic, and food industries that can be prepared from glucose 6-phosphate produced by the enzymatic methods.

EXAMPLES

Example 1: Production of Recombinant Expression Vector Including Polyphosphate-Dependent Glucokinase Gene and Microorganism Transformed with the Recombinant Expression Vector The Dg_ppgk gene of a polyphosphate-dependent glucokinase derived from thermophilic *Deinococcus geothermalis*, was isolated.

Specifically, gene sequences associated with the novel thermophilic and thermoresistant enzyme according to the present invention were primarily screened from the gene sequences registered in Genbank and only the gene sequence derived from the thermophilic microorganism was finally selected therefrom. The registered gene sequence (SEQ ID NO. 1) and the amino acid sequence (SEQ ID NO. 2) of *Deinococcus geothermalis* were analyzed to design a forward primer (SEQ ID NO. 3) and a reverse primer (SEQ ID NO. 4). The corresponding gene was amplified from the *Deinococcus geothermalis* genomic DNA by polymerase chain reaction (PCR) using the synthesized primers. The amplified polyphosphate-dependent glucokinase gene was inserted into plasmid vector pET21a (Novagen) for *E. coli* expression using restriction enzymes NdeI and XhoI to construct a recombinant expression vector (pET21a-Dg_ppgk). The recombinant expression vector was transformed into strain *E. coli* BL21(DE3) by a general transformation technique (see Sambrook et al. 1989) to produce a transformed microorganism.

Example 2: Production of Polyphosphate-Dependent Glucokinase

In this example, a recombinant polyphosphate-dependent glucokinase was produced. First, a culture tube containing 5 ml of LB liquid medium was inoculated with the transformed microorganism. The inoculum was cultured in a shaking incubator at 37° C. until an absorbance of 2.0 at 600 nm was reached. The culture broth was added to LB liquid medium in a flask, followed by main culture. When the absorbance of the culture at 600 nm reached 2.0, 1 mM IPTG was added to induce the expression and production of a recombinant enzyme. The culture temperature was maintained at 37° C. with stirring at 200 rpm.

The recombinant enzyme produced by overexpression was purified by the following procedure. First, the culture broth of the transformed strain was centrifuged at 8,000×g and 4° C. for 20 min and washed twice with 50 mM Tris-Cl buffer (pH 7.5). Then, cells were disrupted using an ultrasonic homogenizer. The cell lysate was centrifuged at 13,000×g and 4° C. for 20 min. The supernatant was collected and purified by His-tag affinity chromatography. The purified recombinant enzyme was dialyzed against buffer for activity measurement (50 mM Tris-Cl, pH 7.5) and was then characterized.

In FIG. 4, M indicates a size marker, CE indicates the crude extract after cell destruction, Ne indicates the enzyme whose gene expression was not induced (negative control), and PE indicates the purified enzyme after gene expression. The purified polyphosphate-dependent glucokinase was found to have a molecular weight of ~30 kDa, as determined by SDS-PAGE (FIG. 4).

Example 3: Analysis of Activity of the Recombinant Polyphosphate-Dependent Glucokinase The purified recombinant polyphosphate-dependent glucokinase derived from the gene constructed based on the gene sequencing result of the sequence registered in Genbank was analyzed for activity.

Glucose (2% (w/v)), $MgCl_2$ (10 mM), sodium hexametaphosphate (1.5% (w/v)), and the purified enzyme (0.3 mg/ml) were mixed together in 50 mM Tris-HCl (pH 7.5) to prepare a reaction composition. The enzymatic reaction was allowed to proceed at 40° C. for 30 min, followed by HPLC. The HPLC conditions were as follows: Aminex HPX-87C (Bio-rad) column, 80° C., 5 mM $H_2SO_4$ solution as mobile phase, and flow rate of 0.6 ml/min. Glucose 6-phosphate was detected and analyzed using a refractive index detector.

As a result, the gene-derived recombinant protein was detected to be active.

Example 4: Analysis of Influences of pH and Temperature on the Activity of the Recombinant Polyphosphate-Dependent Glucokinase 4-1. Analysis of pH Influence The influence of pH on the enzyme activity was investigated. To this end, glucose (2% (w/v)), $MgCl_2$ (10 mM), sodium hexametaphosphate (1.5% (w/v)), and the purified enzyme (0.3 mg/ml) were mixed together in 50 mM buffers (sodium acetate, pH 4-6; potassium phosphate, pH 6-8; Tris-HCl, pH 7-8) to prepare reaction compositions. The enzymatic reaction was allowed to proceed at 40° C. for 30 min, followed by HPLC. The results are shown in FIG. 5. The enzyme showed a maximum activity around pH 8. The activity of the enzyme was found to be higher in the Tris-HCl buffer than in the other buffers (FIG. 5).

4-2. Analysis of Temperature Influence

Changes in the activity of the enzyme according to temperature variation were investigated. To this end, glucose (2% (w/v)), $MgCl_2$ (10 mM), sodium hexametaphosphate (1.5% (w/v)), and the purified enzyme (0.3 mg/ml) were mixed together in 50 mM Tris-HCl (pH 7.5) to prepare a reaction composition. The enzymatic reaction was allowed to proceed at different temperatures of 30° C. to 65° C. for 30 min, followed by HPLC.

The highest activity of the enzyme was observed at 50° C. (FIG. 6).

Example 5: Analysis of Demand of the Recombinant Polyphosphate-Dependent Glucokinase for Metal Ions The polyphosphate-dependent glucokinases reported to date are known to demand metal ions. In this example, the influence of metal ions on the activity of the inventive polyphosphate-dependent glucokinase was investigated. To this end, the inventive enzyme was treated with 10 mM EDTA, followed by dialysis to prepare an enzyme sample.

Glucose (2% (w/v)), metal ions ($NiSO_4$, $CuSO_4$, $MnSO_4$, $CaCl_2$, $ZnSO_4$, $MgSO_4$, $MgCl_2$, $FeSO_4$, NaCl, LiCl, KCl, and $CoCl_2$, 5 mM each), sodium hexametaphosphate (1.5% (w/v)), and the metal ion-free enzyme sample (0.3 mg/ml) were mixed together in 50 mM Tris-HCl (pH 7.5) to prepare reaction compositions. The enzymatic reaction was allowed to proceed at 50° C. for 30 min, followed by HPLC.

The enzyme sample before treatment with metal ions was used as a control. The activity of the control was compared with the activities of the reaction compositions after treatment with metal ions. The magnesium salts were more effective for the production of glucose 6-phosphate by the polyphosphate-dependent glucokinase derived from *Deinococcus geothermalis* than the other metal salts analyzed, as shown in FIG. 7. Particularly, the addition of $MgCl_2$ was confirmed to exhibit the maximum activity. Experiments were conducted at different concentrations of $MgCl_2$. As a result, a higher activity was observed at a concentration of 10 mM (FIG. 8).

Example 6: Temperature Stability

The temperature stability of the polyphosphate-dependent glucokinase was investigated. To this end, the enzyme was heated to different temperatures of 40-70° C. for 6 h, and residual activities were measured, compared, and analyzed.

Glucose (2% (w/v)), $MgCl_2$ (10 mM), sodium hexametaphosphate (1.5% (w/v)), and the purified enzyme (0.3 mg/ml) were mixed together in Tris-HCl (50 mM, pH 7.5) to prepare a reaction composition. The enzymatic reaction was allowed to proceed at 50° C. for 30 min, followed by HPLC.

The results are shown in FIG. 9. The activity of the enzyme was reduced to half of its initial value after 6 h at 40° C. and after 1 h at 50° C.

Example 7: Analysis of Conversion Yields at Different Concentrations of the Substrates The conversion yields of glucose 6-phosphate at different concentrations of the substrates were analyzed to investigate the productivity of glucose 6-phosphate using the inventive purified enzyme.

Glucose (3% and 15% (w/v)), $MgCl_2$ (10 mM), sodium hexametaphosphate (1.5% and 7.5% (w/v)), and the purified enzyme (0.3 mg/ml) were mixed together in Tris-HCl (50 mM, pH 8.0) to prepare reaction compositions. The enzymatic reaction was allowed to proceed at 50° C. for different periods of time, followed by HPLC.

As a result, the use of 3% (w/v) glucose and 1.5% (w/v) sodium hexametaphosphate achieved a conversion yield of 88.5% after reaction for 0.8 h. The use of 15% (w/v) glucose and 7.5% (w/v) sodium hexametaphosphate achieved a conversion yield of 74.2% after reaction for 24 h.

The invention claimed is:

1. A method for producing glucose 6-phosphate comprising contacting a thermoresistant polyphosphate-dependent glucokinase having the amino acid sequence of SEQ ID NO:2 with glucose and polyphosphate at a temperature of 40° C. to 55° C.

2. The method according to claim 1, wherein the glucose is prepared by liquefaction or glycosylation of starch or cellulose.

3. The method according to claim 1, wherein the polyphosphate is sodium hexametaphosphate.

4. The method according to claim 1, wherein glucose 6-phosphate is produced at a temperature of 40° C. to 60° C. and/or a pH of 7 to 9.

5. The method according to claim 1, wherein the composition further comprises magnesium ions.

6. The method according to claim 1, wherein the polyphosphate-dependent glucokinase is present in an amount of 0.1 mg/ml to 0.5 mg/ml.

7. The method according to claim 1, wherein the glucose is present in an amount of 1% to 30% by weight, based on the total volume of the composition.

8. The method according to claim 1, wherein the polyphosphate is present in an amount of 1% to 10% by weight, based on the total volume of the composition.

9. The method according to claim 1, wherein the glucose is prepared by contacting a diastatic enzyme with starch, wherein the diastatic enzyme is selected from alpha-amylases, glucoamylases, alpha-glycosidases, and mixtures thereof.

* * * * *